US012767631B2

(12) United States Patent
Hashikawa et al.

(10) Patent No.: US 12,767,631 B2
(45) Date of Patent: Oct. 20, 2026

(54) METHOD FOR PRODUCING POLYETHER NITRILE

(71) Applicants: HONSHU CHEMICAL INDUSTRY CO., LTD., Tokyo (JP); DAIKIN INDUSTRIES, LTD., Osaka (JP)

(72) Inventors: Akihiro Hashikawa, Wakayama (JP); Tomoaki Shimoda, Wakayama (JP); Yasuhiro Nakano, Osaka (JP)

(73) Assignees: HONSHU CHEMICAL INDUSTRY CO., LTD., Tokyo (JP); DAIKIN INDUSTRIES, LTD., Osaka (JP)

( * ) Notice: Subject to any disclaimer, the term of this patent is extended or adjusted under 35 U.S.C. 154(b) by 283 days.

(21) Appl. No.: 18/709,657

(22) PCT Filed: Oct. 26, 2022

(86) PCT No.: PCT/JP2022/039962
§ 371 (c)(1),
(2) Date: May 13, 2024

(87) PCT Pub. No.: WO2023/090101
PCT Pub. Date: May 25, 2023

(65) Prior Publication Data

US 2025/0019342 A1 Jan. 16, 2025

(30) Foreign Application Priority Data

Nov. 18, 2021 (JP) ................................ 2021-187925

(51) Int. Cl.
*C07C 253/30* (2006.01)
*C08G 65/40* (2006.01)

(52) U.S. Cl.
CPC ................................ *C07C 253/30* (2013.01)

(58) Field of Classification Search
None
See application file for complete search history.

(56) References Cited

U.S. PATENT DOCUMENTS 4,567,248 A 1/1986 Blinne et al.

FOREIGN PATENT DOCUMENTS

| | | | |
|---|---|---|---|
| CN | 112625233 | A | 4/2021 |
| JP | S60147439 | A | 8/1985 |
| JP | S60258250 | A | 12/1985 |
| JP | S6155120 | A | 3/1986 |
| JP | S63189435 | A | 8/1988 |
| JP | H0762085 | A | 3/1995 |
| JP | H0890557 | A | 4/1996 |
| JP | H08259689 | A | 10/1996 |
| JP | H11158264 | A | 6/1999 |
| JP | 2008166077 | A | 7/2008 |

OTHER PUBLICATIONS

International Search Report (ISR) mailed Jan. 17, 2023, issued for International application No. PCT/JP2022/039962. (3 pages).
International Preliminary Report on Patentability, dated May 2, 2024, for corresponding international application PCT/JP2022/039962 (1 page).
Notification Concerning Transmittal of Copy of International Preliminary Report on Patentability, mailed May 30, 2024, for corresponding international application PCT/JP2022/039962 (1 page).
Notification of Transmittal of Copies of Translation of the International Preliminary Report on Patentability, mailed May 30, 2024, for corresponding international application PCT/JP2022/039962 (1 page).
Written Opinion of the International Searching Authority, mailed Jan. 17, 2023, for corresponding international application PCT/JP2022/039962 (3 pages).
Extended European Search Report (EESR) dated Nov. 20, 2025, issued for European counterpart patent application No. EP22895385.7 (11 pages).
Lakshmana Rao V. et al: "Poly(Arylene Ether Nitriles)", Journal of Macromolecular Science: Part C—Polymer Reviews, vol. 42, No. 4, Jan. 12, 2002 (Jan. 12, 2002), pp. 513-540, XP055802006, USISSN: 1532-1797, DOI: 10.1081/MC-120015989 Retrieved from the Internet: URL:https://www.tandfonline.com/doi/pdf/10.1081/MC-120015989> (29 pages).

*Primary Examiner* — Sun Jae Yoo
(74) *Attorney, Agent, or Firm* — Law Office of Katsuhiro Arai

(57) ABSTRACT

A method for producing a polyether nitrile includes allowing an aromatic dihydroxy compound composition (I) and a dihalobenzonitrile compound composition (II) to undergo a polycondensation reaction in the presence of a basic compound. In the method, the aromatic dihydroxy compound composition (I) includes an aromatic dihydroxy compound (I-a) and an aromatic monohydroxy compound (I-b), and contains (I-a) in an amount ranging from 99.0 to 99.995 mol % and (I-b) in an amount ranging from 1 to 0.005 mol % relative to a total amount of (I-a) and (I-b), and the dihalobenzonitrile compound composition (II) includes a dihalobenzonitrile compound (II-a) and a monohalobenzonitrile compound (II-b), and contains (II-a) in an amount ranging from 99.0 to 99.995 mol % and (II-b) in an amount ranging from 1 to 0.005 mol % relative to a total amount of (II-a) and (II-b).

10 Claims, No Drawings

METHOD FOR PRODUCING POLYETHER NITRILE

CROSS-REFERENCE TO RELATED APPLICATIONS

This application is the U.S. National Phase under 35 U.S.C. § 371 of International Application PCT/JP2022/039962, filed Oct. 26, 2022, which claims priority to Japanese Patent Application No. JP2021-187925, filed Nov. 18, 2021. The International Application was published under PCT Article 21 (2) in a language other than English.

TECHNICAL FIELD

The present invention relates to a method for producing a polyether nitrile having a high molecular weight at a practical polymerization rate.

BACKGROUND ART

Aromatic ether copolymers are not only excellent in heat resistance, flame resistance, chemical resistance, and mechanical strength but also are thermoplastic and can be melt-molded by heating, and thus can provide various molded articles such as filaments, films, sheets, tubes, pipes, and round bars through molding methods such as injection molding, extrusion molding, and heat compression molding and are useful resins.

(Co)polymers are generally heated, melted, and kneaded with resin materials added and then formed into molding materials (resin compositions) such as pellets and chips, which are processed into various molded articles, but aromatic ether copolymers are useful as base resins for molding materials (resin compositions).

However, polyether nitriles polymerized using an aromatic dihydroxy compound and a dihalobenzonitrile compound as raw materials (e.g., PTLs 1 and 2) have a problem in that their polymerization rate and achievable molecular weight are greatly affected by the purity of each raw material and the content of impurities.

CITATION LIST

Patent Literature

PTL 1: Japanese Unexamined Patent Application Publication No. 60-147439
PTL 2: Japanese Unexamined Patent Application Publication No. 61-055120

SUMMARY OF INVENTION

Technical Problem

An object of the present invention is to provide a method for producing a polyether nitrile having a high molecular weight at a practical polymerization rate.

Solution to Problem

To achieve the above object, the present inventors have conducted intensive studies and found that a high-molecular-weight polyether nitrile can be obtained at a practical polymerization rate by performing polymerization using raw materials each containing a specific compound in raw material impurities in an amount in a specific range, thereby completing the present invention.

The present invention is as follows.

1. A method for producing a polyether nitrile, including allowing an aromatic dihydroxy compound composition (I) and a dihalobenzonitrile compound composition (II) to undergo a polycondensation reaction in the presence of a basic compound,
   wherein the aromatic dihydroxy compound composition (I) includes an aromatic dihydroxy compound (I-a) and an aromatic monohydroxy compound (I-b), and contains (I-a) in an amount ranging from 99.0 to 99.995 mol % and (I-b) in an amount ranging from 1 to 0.005 mol % relative to a total amount of (I-a) and (I-b), and
   the dihalobenzonitrile compound composition (II) includes a dihalobenzonitrile compound (II-a) and a monohalobenzonitrile compound (II-b), and contains (II-a) in an amount ranging from 99.0 to 99.995 mol % and (II-b) in an amount ranging from 1 to 0.005 mol % relative to a total amount of (II-a) and (II-b).
2. The method for producing a polyether nitrile according to 1., wherein the aromatic dihydroxy compound (I-a) is a compound represented by general formula (1) below, the aromatic monohydroxy compound (I-b) is a compound represented by general formula (2) below, the dihalobenzonitrile compound (II-a) is a compound represented by general formula (3) below, and the monohalobenzonitrile compound (II-b) is a compound represented by general formula (4) below.

[Chem. 1]

HO—R—OH (1)

(In the formula, R represents a divalent group represented by general formula (1a) below or general formula (1b) below.)

[Chem. 2]

(1a)

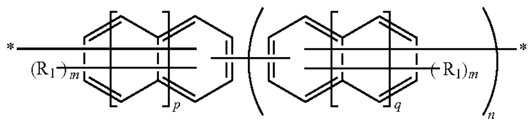

(In the formula, each $R_1$ independently represents a linear or branched alkyl group having 1 to 6 carbon atoms, a cyclic alkyl group having 5 or 6 carbon atoms, a phenyl group, a phenoxy group, or a phenylalkyl group having 7 to 10 carbon atoms, m represents an integer of 0 to 4, n represents 0 or 1, p and q each independently represent 0, 1, or 2, and each * represents a bonding position.)

[Chem. 3]

(1b)

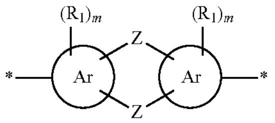

(In the formula, $R_1$ and m are as defined in general formula (1a), Y represents an oxygen atom, a sulfur atom, a sulfonyl group, a carbonyl group, an alkylidene group having 1 to 15 carbon atoms, a fluorine-containing alkylidene group having 2 to 15 carbon atoms, a cycloalkylidene group having 5 to 15 carbon atoms, a phenylmethylidene group, a phenylethylidene group, a phenylene group, or a fluorenylidene group, Z represents an oxygen atom, a sulfur atom, or non-bridging, each Ar independently represents an aryl group having 6 to 8 carbon atoms, and each * represents a bonding position.)

[Chem. 4]

(2)

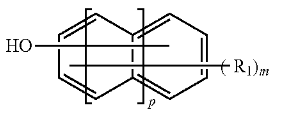

(In the formula, $R_1$, m, and p are as defined in general formula (1a).)

[Chem. 5]

(3)

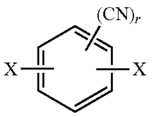

(In the formula, each X independently represents a halogen atom, and r represents an integer of 1 to 4.)

[Chem. 6]

(4)

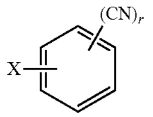

(In the formula, X and r are as defined in general formula (3).)

3. The method for producing a polyether nitrile according to 2., wherein R in the compound represented by general formula (1) is general formula (1a') below or general formula (1a") below, p in the compound represented by general formula (2) is 0, and r in the compound represented by general formula (3) and the compound represented by general formula (4) is 1.

[Chem. 7]

(1a')

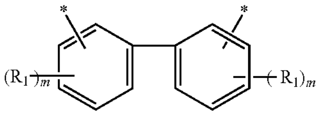

(In the formula, $R_1$, m, and * are as defined in general formula (1a).)

[Chem. 8]

(1a")

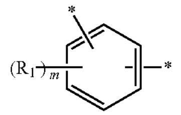

In the formula, $R_1$, m, and * are as defined in general formula (1a).)

4. The method for producing a polyether nitrile according to 2., wherein the aromatic dihydroxy compound (I-a) is 4,4'-biphenol, the aromatic monohydroxy compound (I-b) is phenol, the dihalobenzonitrile compound (II-a) is 2,6-dichlorobenzonitrile, and the monohalobenzonitrile compound (II-b) is 2-chlorobenzonitrile.
5. The method for producing a polyether nitrile according to 1., wherein in the aromatic dihydroxy compound composition (I), a content of the aromatic dihydroxy compound (I-a) relative to the entire aromatic dihydroxy compound composition (I) is 99.0 wt % or more, and in the dihalobenzonitrile compound composition (II), a content of the dihalobenzonitrile compound (II-a) relative to the entire dihalobenzonitrile compound composition (II) is 99.0 wt % or more.
6. The method for producing a polyether nitrile according to any one of 1. to 5., wherein a resulting polyether nitrile has a reduced viscosity of 2.0 or more.

Advantageous Effects of Invention

The method for producing a polyether nitrile according to the present invention can provide a high-molecular-weight polyether nitrile at a practical polymerization rate, and thus is very useful.

DESCRIPTION OF EMBODIMENTS

The present invention is a method for producing a polyether nitrile, including allowing an aromatic dihydroxy compound composition (I) and a dihalobenzonitrile compound composition (II) to undergo a polycondensation reaction in the presence of a basic compound. The aromatic dihydroxy compound composition (I) includes an aromatic dihydroxy compound (I-a) and an aromatic monohydroxy compound (I-b), and contains (I-a) in an amount ranging from 99.0 to 99.995 mol % and (I-b) in an amount ranging from 1 to 0.005 mol % relative to the total amount of (I-a) and (I-b). The dihalobenzonitrile compound composition (II) includes a dihalobenzonitrile compound (II-a) and a monohalobenzonitrile compound (II-b), and contains (II-a) in an amount ranging from 99.0 to 99.995 mol % and (II-b) in an amount ranging from 1 to 0.005 mol % relative to the total amount of (II-a) and (II-b).

Although both the aromatic monohydroxy compound and the monohalobenzonitrile compound act as agents for stopping the polycondensation reaction of the polyether nitrile, using the aromatic dihydroxy compound composition (I) and the dihalobenzonitrile compound composition (II) whose contents are within the above ranges can provide a high-molecular-weight polyether nitrile at a practical polymerization rate.

Aromatic Dihydroxy Compound Composition (I)

The aromatic dihydroxy compound composition (I) in the present invention includes an aromatic dihydroxy compound (I-a) and an aromatic monohydroxy compound (I-b), and contains (I-a) in an amount ranging from 99.0 to 99.995 mol % and (I-b) in an amount ranging from 1 to 0.005 mol % relative to the total amount of (I-a) and (I-b).

In the aromatic dihydroxy compound composition (I) in the present invention, the content of the aromatic dihydroxy compound (I-a) relative to the total amount of (I-a) and (I-b) is preferably in the range of 99.5 to 99.995 mol %, more preferably in the range of 99.6 to 99.995 mol %, particularly preferably in the range of 99.7 to 99.995 mol %.

In the aromatic dihydroxy compound composition (I) in the present invention, the content of the aromatic monohydroxy compound (I-b) relative to the total amount of (I-a) and (I-b) is preferably in the range of 0.5 to 0.005 mol %, more preferably in the range of 0.4 to 0.005 mol %, particularly preferably in the range of 0.3 to 0.005 mol %.

The aromatic dihydroxy compound composition (I) may contain impurity components other than the aromatic dihydroxy compound (I-a) and the aromatic monohydroxy compound (I-b). The content of the aromatic dihydroxy compound (I-a) relative to the entire aromatic dihydroxy compound composition (I) is preferably 99.0 wt % or more, more preferably 99.5 wt % or more, still more preferably 99.7 wt % or more, particularly preferably 99.8 wt % or more.

Aromatic Dihydroxy Compound (I-a)

The aromatic dihydroxy compound (I-a) in the present invention includes all aromatic compounds having two hydroxy groups, among which a compound represented by general formula (1) below is preferred.

[Chem. 9]

HO—R—OH (1)

(In the formula, R represents a divalent group represented by formula (1a) below or formula (1b) below.)

[Chem. 10]

(1a)

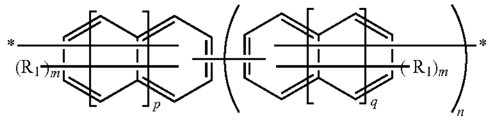

(In the formula, each $R_1$ independently represents a linear or branched alkyl group having 1 to 6 carbon atoms, a cyclic alkyl group having 5 or 6 carbon atoms, a phenyl group, a phenoxy group, or a phenylalkyl group having 7 to 10 carbon atoms, m represents an integer of 0 to 4, n represents an integer of 0 or 1, p and q each independently represent 0, 1, or 2, and each * represents a bonding position.)

[Chem. 11]

(1b)

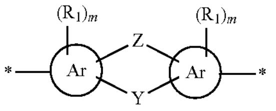

(In the formula, $R_1$ and m are as defined in general formula (1a), Y represents an oxygen atom, a sulfur atom, a sulfonyl group, a carbonyl group, an alkylidene group having 1 to 15 carbon atoms, a fluorine-containing alkylidene group having 2 to 15 carbon atoms, a cycloalkylidene group having 5 to 15 carbon atoms, a phenylmethylidene group, a phenylethylidene group, a phenylene group, or a fluorenylidene group, Z represents an oxygen atom, a sulfur atom, or non-bridging, each Ar independently represents an aryl group having 6 to 8 carbon atoms, and each * represents a bonding position.)

Each $R_1$ in general formula (1a) independently represents a linear or branched alkyl group having 1 to 6 carbon atoms, a cyclic alkyl group having 5 or 6 carbon atoms, a phenyl group, a phenoxy group, or a phenylalkyl group having 7 to 10 carbon atoms, preferably a linear or branched alkyl group having 1 to 4 carbon atoms, a cyclic alkyl group having 5 or 6 carbon atoms, or a phenyl group, more preferably a linear or branched alkyl group having 1 to 4 carbon atoms or a phenyl group, particularly preferably an alkyl group having 1 carbon atom, that is, a methyl group.

"Phenylalkyl group having 7 to 10 carbon atoms" means a group represented as phenyl-C1 to C4 alkylene. "C1 to C4 alkylene" means a linear alkylene group having 1 to 4 carbon atoms or a branched alkylene group having 3 or 4 carbon atoms. The alkylene group having 1 to 4 carbon atoms is preferably an alkylene group having 1 carbon atom (a methylene group) or a branched alkylene group having 3 carbon atoms, more preferably a methylene group or an isopropylidene group.

In general formula (1a), m represents an integer of 0 to 4, preferably an integer 0, 1, or 2, more preferably 0 or 1, particularly preferably 0.

In general formula (1a), n represents 0 or 1, preferably 1.

In general formula (1a), p and q each independently represent 0, 1, or 2, preferably 0 or 1, particularly preferably 0.

Formula (Ia) above where n is 1 and p and q are 0 is represented as general formula (1a').

[Chem. 12]

(1a')

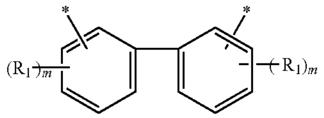

(In the formula, $R_1$, m, and * are as defined in general formula (1a).)

In general formula (1a'), the position of bonding to OH in general formula (1) is preferably the ortho or para position, particularly preferably the para position, with respect to the position of direct bonding between the two benzene rings. When m is 1 or 2, the bonding position of $R_1$ is preferably the meta position with respect to the position of direct bonding between the two benzene rings. Preferred examples of $R_1$ and m are the same as those in general formula (1a).

General formula (1a) where n, p, and q are 0 is represented as general formula (1a") below.

[Chem. 13]

(1a")

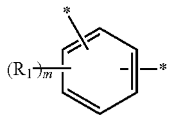

(In the formula, $R_1$, m, and * are as defined in general formula (1a).)

In general formula (1a"), the position of bonding to OH in general formula (1) is preferably the para or meta position, particularly preferably the para position, with respect to the other bonding position. Preferred examples of $R_1$ and m are the same as those in general formula (1a). $R_1$ and m in general formula (1b) are as defined in general formula (1a), and preferred examples are also the same.

Y in general formula (1b) represents an oxygen atom, a sulfur atom, a sulfonyl group, a carbonyl group, an alkylidene group having 1 to 15 carbon atoms, a fluorine-containing alkylidene group having 2 to 15 carbon atoms, a cycloalkylidene group having 5 to 15 carbon atoms, a phenylmethylidene group, a phenylethylidene group, a phenylene group, or a fluorenylidene group, and the cycloalkylidene group having 5 to 15 carbon atoms may include a branched-chain alkyl group. Specific examples of the cycloalkylidene group include a cyclopentylidene group (5 carbon atoms), a cyclohexylidene group (6 carbon atoms), a 3-methylcyclohexylidene group (7 carbon atoms), a 4-methylcyclohexylidene group (7 carbon atoms), a 3,3,5-trimethylcyclohexylidene group (9 carbon atoms), a cycloheptylidene group (7 carbon atoms), and a cyclododecanylidene group (12 carbon atoms).

Y in general formula (1b) is preferably a sulfonyl group, a carbonyl group, an alkylidene group having 1 to 6 carbon atoms, a fluorine-containing alkylidene group having 2 to 6 carbon atoms, a cycloalkylidene group having 5 to 12 carbon atoms, a phenylmethylidene group, a phenylethylidene group, a phenylene group, or a fluorenylidene group, more preferably a sulfonyl group, a carbonyl group, an alkylidene group having 1 to 3 carbon atoms, a fluorine-containing alkylidene group having 2 or 3 carbon atoms, a cycloalkylidene group having 6 to 12 carbon atoms, a phenylmethylidene group, or a fluorenylidene group, still more preferably an alkylidene group having 3 carbon atoms, that is, a propylidene group, a fluorine-containing alkylidene group having 3 carbon atoms, that is, a fluorine-containing propylidene group, a cycloalkylidene group having 6 to 12 carbon atoms, or a fluorenylidene group, particularly preferably a 2,2'-isopropylidene group, a 2,2'-hexafluoroisopropylidene group, a cyclohexylidene group, a 3,3,5-trimethylcyclohexylidene group, a cyclododecanylidene group, or a fluorenylidene group.

Z in general formula (1b) represents an oxygen atom, a sulfur atom, or non-bridging, preferably an oxygen atom or non-bridging, more preferably non-bridging.

Ar in general formula (1b) represents an aryl group having 6 to 8 carbon atoms, more preferably an aryl group having 6 carbon atoms.

R in general formula (1) is preferably a divalent group represented by general formula (1a), more preferably a divalent group represented by general formula (1a') or a divalent group represented by general formula (1a"), particularly preferably a divalent group represented by general formula (1a').

Specific examples of the aromatic dihydroxy compound (I-a) in the present invention include hydroquinone, resorcin, 2-phenylhydroquinone, 4,4'-biphenol, 3,3'-biphenol, 2,6-dihydroxynaphthalene, 2,7-dihydroxynaphthalene, 1,1'-bi-2-naphthol, 2,2'-bi-1-naphthol, 1,3-bis[1-methyl-1-(4-hydroxyphenyl)ethyl]benzene, 1,4-bis[1-methyl-1-(4-hydroxyphenyl)ethyl]benzene, 1,3-(4-hydroxybenzoylbenzene), 1,4-(4-hydroxybenzoylbenzene), 1,3-bis(4-hydroxyphenoxy)benzene, 1,4-bis(4-hydroxyphenoxy)benzene, 1,4-bis(4-hydroxyphenyl)benzene, 1,3-bis(4-hydroxyphenyl)benzene, 4,4'-isopropylidene biphenol (Bis-A), 2,2-bis(4-hydroxyphenyl)-1,1,1,3,3,3-hexafluoropropane, 4,4'-bishydroxybenzophenone, 4,4'-bishydroxydiphenylsulfone, 4,4'-dihydroxydiphenyl ether, bis(4-hydroxyphenyl)methane, 9,9-bis(4-hydroxyphenyl)fluorene, 9,9-bis(3-phenyl-4-hydroxyphenyl)fluorene, 9,9-bis(3,5-diphenyl-4-hydroxyphenyl)fluorene, 9,9-bis(4-hydroxy-3-methylphenyl)fluorene, 9,9-bis(4-hydroxy-3,5-dimethylphenyl)fluorene, 9,9-bis(4-hydroxy-3-cyclohexylphenyl)fluorene, 4,4'-isopropylidene bis(2-phenylphenol), bisphenol Z (1,1-bis(4-hydroxyphenyl)cyclohexane), bisphenol TMC (1,1-bis(4-hydroxyphenyl)-3,3,5-trimethylcyclohexane), 1,1-bis(4-hydroxyphenyl)cyclododecane, and 1,1-bis(4-hydroxyphenyl)-1-phenylethane. At least one of these compounds is used. These may be used alone or may be used in combination of two or more.

Of these, at least one selected from hydroquinone, resorcin, and 4,4'-biphenol is preferred, hydroquinone, resorcin, or 4,4'-biphenol is more preferred, and 4,4'-biphenol is particularly preferred.

Aromatic Monohydroxy Compound (I-b)

The aromatic monohydroxy compound (I-b) in the present invention includes all aromatic compounds having one hydroxy group, among which a compound represented by general formula (2) below is preferred.

[Chem. 14]

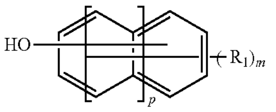

(2)

(In the formula, $R_1$, m, and p are as defined in general formula (1a).)

Preferred examples of $R_1$, m, and p in general formula (2) are the same as those in general formula (1a).

Typically, an aromatic monohydroxy compound is used as a raw material for a target aromatic dihydroxy compound or as a purification solvent in some cases or is produced as a by-product during the reaction, and is contained in a specific amount as an impurity in the produced aromatic dihydroxy compound depending on the reaction and purification conditions.

Specific examples of the aromatic monohydroxy compound (I-b) in the present invention include phenol, cresol, butylated phenol, phenylphenol, phenoxyphenol, benzylphenol, cumylphenol, and naphthol.

In the production method according to the present invention, the aromatic dihydroxy compound composition (I) needs to satisfy the above-described content only when the polycondensation reaction is performed. That is, for the aromatic dihydroxy compound composition (I), a composition satisfying the above-described content may be provided in advance and supplied to a polycondensation reactor, or a plurality of aromatic dihydroxy compound compositions (I) having different content ratios may be supplied into a polycondensation reactor such that the content ratio of the entire aromatic dihydroxy compound composition (I) contained in the reactor satisfies the above-described content.

Dihalobenzonitrile Compound Composition (II)

The dihalobenzonitrile compound composition (II) in the present invention includes a dihalobenzonitrile compound (II-a) and a monohalobenzonitrile compound (II-b), and contains (II-a) in an amount ranging from 99.0 to 99.995 mol % and (II-b) in an amount ranging from 1 to 0.005 mol % relative to the total amount of (II-a) and (II-b).

In the dihalobenzonitrile compound composition (II) in the present invention, the content of the dihalobenzonitrile compound (II-a) relative to the total amount of (II-a) and (II-b) is preferably in the range of 99.5 to 99.995 mol %, more preferably in the range of 99.6 to 99.995 mol %, particularly preferably in the range of 99.7 to 99.995 mol %.

In the dihalobenzonitrile compound composition (II) in the present invention, the content of the monohalobenzonitrile compound (II-b) relative to the total amount of (II-a) and (II-b) is preferably in the range of 0.5 to 0.005 mol %, more preferably in the range of 0.4 to 0.005 mol %, particularly preferably in the range of 0.3 to 0.005 mol %.

The dihalobenzonitrile compound composition (II) in the present invention may contain impurity components other than the dihalobenzonitrile compound (II-a) and the monohalobenzonitrile compound (II-b). The content of the dihalobenzonitrile compound (II-a) relative to the entire dihalobenzonitrile compound composition (II) is preferably 99.0 wt % or more, more preferably 99.5 wt % or more, still more preferably 99.7 wt % or more, particularly preferably 99.8 wt % or more.

Dihalobenzonitrile Compound (II-a)

The dihalobenzonitrile compound (II-a) includes all benzonitrile compounds having two halogen groups, among which a compound represented by general formula (3) below is preferred.

[Chem. 15]

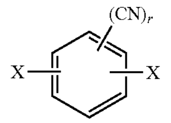

(3)

(In the formula, each X independently represents a halogen atom, and r represents an integer of 1 to 4.)

Each X in general formula (3) above independently represents a halogen atom, preferably independently represents a chlorine atom, a bromine atom, or an iodine atom, more preferably independently represents a chlorine atom or a bromine atom, particularly preferably represents a chlorine atom.

In general formula (3) above, r represents an integer of 1 to 4, preferably 1 or 2, more preferably 1. When r is 1, a structural configuration in which halogen atoms are bonded to both the ortho positions with respect to the cyano group is preferred.

Specific examples of the dihalobenzonitrile compound (II-a) in the present invention include 2,6-difluorobenzonitrile, 2,5-difluorobenzonitrile, 2,4-difluorobenzonitrile, 2,6-dichlorobenzonitrile, 2,5-dichlorobenzonitrile, 2,4-dichlorobenzonitrile, 2,6-dibromobenzonitrile, 2,5-dibromobenzonitrile, 2,4-dibromobenzonitrile, 2,6-dinitrobenzonitrile, 2,5-dinitrobenzonitrile, 2,4-dinitrobenzonitrile, and 1,4-dichloro-2,5-dicyanobenzene. The dihalobenzonitrile compound (II-a) may also be a reactive derivative thereof. Of these, 2,6-difluorobenzonitrile and 2,6-dichlorobenzonitrile are suitable for use from the viewpoint of, for example, reactivity and economic efficiency. These compounds may also be used in combination of two or more.

Examples of the reactive derivative include, in the case of structures derived from 2,6-dihalobenzonitrile, compounds that can react with aromatic dihydroxy compounds as represented by the following formulae, and these mean compounds derived from the reactions between two 2,6-dihalobenzonitriles and between 2,6-dihalobenzonitrile and an aromatic dihydroxy compound.

[Chem. 16]

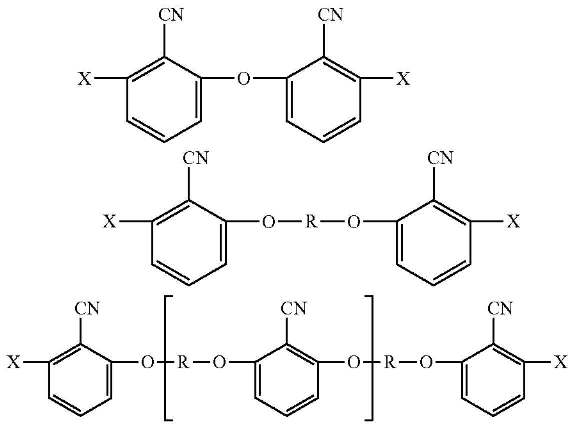

(In the formulae, R is as defined in general formula (1), and X is as defined in general formula (3).)

Monohalobenzonitrile Compound (II-b)

The monohalobenzonitrile compound (II-b) in the present invention includes all benzonitrile compounds having one halogen group, among which a compound represented by general formula (4) below is preferred.

[Chem. 17]

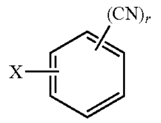

(4)

(In the formula, X and r are as defined in general formula (3).)

Typically, the dihalobenzonitrile compound (II-a) is produced by a known method such as ammoxidation of a halogenated alkylbenzene such as dihalotoluene or halogenation of benzonitrile. The monohalobenzonitrile compound (II-b) is derived from a monohalogen impurity contained in each raw material or produced as a by-product in the reaction, and is contained in a specific amount as an impurity in the produced dihalobenzonitrile compound (II-a) depending on, for example, the purification conditions.

Specific examples of the monohalobenzonitrile compound (II-b) in the present invention include 3-fluorobenzonitrile, 2-bromobenzonitrile, 2-chlorobenzonitrile, 3-chlorobenzonitrile, 2-fluorobenzonitrile, and 3-bromobenzonitrile.

In the production method according to the present invention, the dihalobenzonitrile compound composition (II) needs to satisfy the above-described content only when the polycondensation reaction is performed. That is, for the dihalobenzonitrile compound composition (II), a composition satisfying the above-described content may be provided in advance and supplied to a polycondensation reactor, or a plurality of dihalobenzonitrile compound compositions (II) having different content ratios may be supplied into a polycondensation reactor such that the content ratio of the entire dihalobenzonitrile compound composition (II) contained in the reactor satisfies the above-described content.

When the compound represented by general formula (1) as the aromatic dihydroxy compound (I-a) in the aromatic dihydroxy compound composition (I) and the compound represented by general formula (3) as the dihalobenzonitrile compound (II-a) in the dihalobenzonitrile compound composition (II) are allowed to undergo a polycondensation reaction in the presence of a basic compound, a polyether nitrile having a repeating unit represented by general formula (5) below is obtained. The reaction formula in this case is shown below.

[Chem. 18]

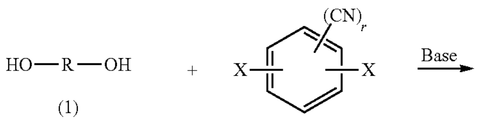

(1)

(3)

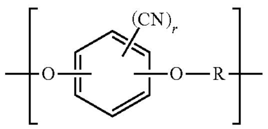

(5)

(In the formula, R is as defined in general formula (1), and X and r are as defined in general formula (3).)

Alternatively, the polycondensation reaction may be performed using a presynthesized alkali metal salt of the aromatic dihydroxy compound composition (I) and the dihalobenzonitrile compound composition (II).

In producing the polyether nitrile, the polycondensation reaction may be performed through divided steps of an oligomer formation step (A) and a polymerization step (B), in which the reaction is performed in different ways, or through a single undivided step.

The oligomer formation step (A) is a step of allowing the aromatic dihydroxy compound composition (I) and the dihalobenzonitrile compound composition (II) to undergo a polycondensation reaction in the presence of a basic compound to form an oligomer. The oligomer in this case is not particularly limited, and a polycondensation reaction product having a polymer reduced viscosity of about less than 1 is referred to as an oligomer.

The polymer formation step (B) is a step of further subjecting the oligomer obtained in the step (A) to the polycondensation reaction to form a polymer. As the oligomer at this time, the polycondensation reaction solution in the step (A) can be used as it is, or an oligomer isolated by additionally performing the step (A) can also be used.

The polycondensation reaction involves an operation to remove water generated during a desalting reaction out of the system. The method of the operation is, for example, a method in which the reaction is run at a temperature at which the desalting reaction proceeds in the presence of a solvent that forms an azeotrope with water, and during the reaction, water is distilled off the reaction mixture by means of the solvent that forms an azeotrope with water. This allows the reaction to be maintained in a substantially anhydrous state. The temperature at which the desalting reaction starts is typically around 130° C., while depending on the raw materials. For example, in the case of using 4,4'-biphenol as the aromatic dihydroxy compound (I-a) in the aromatic dihydroxy compound composition (I), 2,6-dichlorobenzonitrile as the dihalobenzonitrile compound (II-a) in the dihalobenzonitrile compound composition (II), potassium carbonate, sulfolane (boiling point, 285° C.) as an aprotic solvent, and toluene as the solvent that forms an azeotrope with water, the reaction temperature is preferably in the range of 130° C. to 170° C.

When the reaction is continued, it is preferable to maintain the reaction system in a substantially anhydrous state while removing water produced as a result of the reaction. When the water produced is not sufficiently removed, the water may react with the components of the dihalobenzonitrile compound composition (II) to form a by-product having a phenol skeleton, resulting in the production of a low-molecular-weight product alone. That is, to obtain a high-molecular-weight polyether nitrile, the reaction system preferably contains substantially no water, preferably less than 0.5 wt % of water.

The polycondensation reaction is performed in an inert atmosphere, such as a nitrogen atmosphere, at atmospheric pressure, but may also be performed under increased pressure or reduced pressure.

Amount of Raw Material Used

In the production method according to the present invention, the aromatic dihydroxy compound composition (I) is used at a molar ratio preferably in the range of 0.99 to 1.005, more preferably in the range of 0.995 to 1.005, still more preferably in the range 0.998 to 1.002, particularly preferably in the range of 0.999 to 1.001, relative to the dihalobenzonitrile compound composition (II). To maximize the polymerization rate in the above step (B), the aromatic dihydroxy compound composition (I) and the dihalobenzonitrile compound composition (II) are preferably used at a molar ratio of substantially 1.000.

When the aromatic dihydroxy compound composition (I) and the dihalobenzonitrile compound composition (II) are respectively assumed to be the aromatic dihydroxy compound (I-a) and the dihalobenzonitrile compound (II-a) with 100% purity and used at a molar ratio of substantially 1.000, if the contents of the aromatic monohydroxy compound (I-b) and the monohalobenzonitrile compound (II-b), which are impurities thereof, are within the range of the present invention, a high-molecular-weight polymer having a degree of polymerization at which the number of repetitions represented by general formula (5) is 94 or more can be produced at a practical polymerization rate.

The degree of polymerization of 94 or more is a value at which the polymer reduced viscosity of a parachlorophenol solution at 40° C. is 2 or more when the aromatic dihydroxy compound (I-a) is 4,4'-biphenol and the dihalobenzonitrile compound (II-a) is 2,6-dihalobenzonitrile.

If the contents of the aromatic monohydroxy compound (I-b) and the monohalobenzonitrile compound (II-b) exceed 1 mol %, the upper limit of the present invention, the polymerization rate will be low, and even if the polymerization is continued for a long period of time, only a degree of polymerization at which the number of repetitions represented by general formula (3) is less than 94 can be achieved.

Basic Compound

The basic compound may be any organic or inorganic compound as long as it promotes the desalting polycondensation reaction and does not affect the quality, but is preferably an inorganic compound, especially preferably an alkali metal compound or an alkaline-earth metal compound, particularly preferably an alkali metal compound.

Organic bases include tetramethylammonium hydroxide, triethylamine, N,N-diisopropylethylamine, 1,1,3,3-tetramethylguanidine (TMG), N,N-dimethyl-4-aminopyridine (DMAP), 2,6-lutidine, pyridine, 1,8-diazabicyclo[5.4.0]-7-undecene (DBU), 1,5-diazabicyclo[4.3.0]-5-nonene (DBN), 7-methyl-1,5,7-triazabicyclo[4.4.0]dec-5-ene (MTBD), 1,5,7-triazabicyclo[4.4.0]dec-5-ene (TBD), 1,8-bis(dimethylaminonaphthalene) (DMAN), 1,4-diazabicyclo[2.2.2]octane (DABCO), tert-butylimino-tri(pyrrolidino)phosphorane, tert-butylimino-tris(dimethylamino)phosphorane, 2-tert-butylimino-2-diethylamino-1,3-dimethylperhydro-1,3,2-diazaphosphorine, tert-octylimino-tris(dimethylamino)phosphorane, phosphazene base $P_2$-Et, phosphazene base $P_2$-t-Bu, phosphazene base $P_3$-t-Bu, phosphazene base $P_4$-t-Bu, and phosphazene base $P_4$-t-Oct.

Among inorganic bases, alkali metal compounds include alkali metals such as lithium, rubidium, cesium, potassium, and sodium; alkali metal hydrides such as lithium hydride, rubidium hydride, cesium hydride, potassium hydride, and sodium hydride; alkali metal hydroxides such as lithium hydroxide, rubidium hydroxide, cesium hydroxide, potassium hydroxide, and sodium hydroxide; alkali metal carbonates such as lithium carbonate, rubidium carbonate, cesium carbonate, potassium carbonate, and sodium carbonate; and alkali metal hydrogen carbonates such as lithium hydrogen carbonate, rubidium hydrogen carbonate, cesium hydrogen carbonate, potassium hydrogen carbonate, and sodium hydrogen carbonate. These may be used alone or in combination of two or more.

By using these alkali metal compounds having a specific surface area of 0.3 $m^2/g$ or more, the desalting polycondensation reaction can be performed with high efficiency. The specific surface area of the alkali metal compound catalyst is preferably 0.8 $m^2/g$ or more, more preferably 1.2 $m^2/g$ or more. By using an alkali metal compound having a larger specific surface area, the chance of contact between the catalyst and the reaction raw materials is further increased, and the desalting polycondensation reaction can be performed with higher efficiency. When the specific surface area is smaller than 0.3 $m^2/g$, the desalting polycondensation reaction cannot be performed with sufficiently high efficiency unless the amount of catalyst is increased, but an increase in the amount of catalyst is not preferred because the polymer quality is affected.

From the above, the basic compound in the production method according to the present invention is preferably an alkali metal carbonate such as lithium carbonate, rubidium carbonate, cesium carbonate, potassium carbonate, or sodium carbonate, more preferably lithium carbonate, potassium carbonate, or sodium carbonate, particularly preferably potassium carbonate or sodium carbonate having a specific surface area of 0.3 $m^2/g$ or more from the viewpoint of availability.

The amount of basic compound used in the production method according to the present invention, for example, in the case of an alkali metal compound, is usually preferably at least 2 times that of the aromatic dihydroxy compound composition (I) on a molar basis in terms of alkali metal ions contained, but side reactions such as ether bond cleavage will occur during the polymerization if a large excess of the alkali metal compound is used. Thus, the amount used is more preferably in the range of 2 to 4 times, still more preferably in the range of 2 to 2.4 times, particularly preferably in the range of 2 to 2.2 times, on a molar basis.

Solvent

In the production method according to the present invention, a reaction solvent can be used, and it is preferable to use an aprotic solvent as the reaction solvent.

Specific examples of the aprotic solvent include N,N-dimethylacetamide, N,N-dimethylformamide, N-methyl-2-pyrolidone, 1,3-dimethyl-2-imidazolidinone, y-butyrolactone, sulfolane, dimethyl sulfoxide, diethyl sulfoxide, dimethyl sulfone, diethyl sulfone, diisopropyl sulfone, diphenyl sulfone, diphenyl ether, benzophenone, dialkoxybenzenes (the number of carbon atoms in the alkoxy group, 1 to 4), and trialkoxybenzenes (the number of carbon atoms in the alkoxy group, 1 to 4). Among these solvents, high-permittivity polar organic solvents such as N-methyl-2-pyrolidone, N,N-dimethylacetamide, sulfolane, diphenyl sulfone, and dimethyl sulfoxide are particularly suitable for use. These may be used alone or in combination of two or more.

The amount of aprotic solvent used is not particularly limited as long as the raw materials are homogeneously dissolved and the alkali metal salt is stirred and dispersed well. Any amount that maximizes the volume efficiency of a polymerization vessel may be chosen according to the raw materials used and the target polymer. Typically, the amount is chosen in the range of 0.5 to 20 times the total weight of the raw materials and the alkali metal salt.

Specific examples of the solvent that forms an azeotrope with water include aromatic hydrocarbons such as benzene, toluene, xylene, hexane, cyclohexane, octane, chlorobenzene, dioxane, tetrahydrofuran, anisole, and phenetole. These may be used alone or in combination of two or more.

When the solvent that forms an azeotrope with water is used, it is preferable to use the solvent that forms an azeotrope with water in an amount in the range of 1 to 100 parts by weight relative to 100 parts by weight of the aprotic solvent, more preferably in the range of 1 to 10 parts by weight, still more preferably in the range of 2 to 5 parts by weight, from the viewpoint of volume efficiency and solvent recovery.

Reaction Temperature

The reaction temperature in the polycondensation reaction is in the range of 140° C. to 300° C. Within this range, the reaction may be continued at a constant temperature, or the temperature may be increased as the polycondensation reaction proceeds.

When the polycondensation reaction is performed through divided steps of the oligomer formation step (A) and the polymerization step (B), the reaction temperature in the oligomer formation step (A) is preferably in the range of 140° C. to 200° C., more preferably in the range of 150° C. to 170° C., still more preferably in the range of 155° C. to 165° C., and the reaction temperature in the polymerization step (B) is preferably in the range of 200° C. to 300° C., more preferably in the range of 210° C. to 270° C., still more preferably in the range of 210° C. to 240° C., particularly preferably in the range 215° C. to 230° C.

For example, in the case of using 4,4'-biphenol as the aromatic dihydroxy compound (I-a) in the aromatic dihydroxy compound composition (I), 2,6-dichlorobenzonitrile as the dihalobenzonitrile compound (II-a) in the dihalobenzonitrile compound composition (II), potassium carbonate, sulfolane (boiling point, 285° C.) as an aprotic solvent, and toluene as the solvent that forms an azeotrope with water, the reaction temperature is preferably in the range of 190° C. to 280° C.

The reaction time of the polycondensation reaction varies depending on the reaction conditions and the raw materials used, but is typically 3 to 20 hours.

When the polycondensation reaction is performed through divided steps of the oligomer formation step (A) and the polymerization step (B), the reaction time of the step (A), while the reaction is preferably continued until carbon dioxide and water are not substantially produced, is not particularly limited. It is typically 1 to 6 hours, preferably about 2 to 4 hours. The reaction time of the step (B) is 0.5 to 3 hours, preferably 0.5 to 2.5 hours, still more preferably 0.5 to 2 hours, from the time when the final polymerization temperature is reached.

(Treatment after Reaction)

After completion of the polycondensation reaction, the polycondensation reaction product is taken out from the reactor, solidified by cooling, then pulverized, and subjected to subsequent cleaning, drying, and molding material (pellet or chip) production steps; alternatively, the product taken out from the reactor may be directly put into a cleaning tank in the cleaning step, or a solvent for use in the cleaning step described below may be poured into the reactor after completion of the polycondensation reaction to transfer the product in slurry form or wax form to the cleaning step.

The cleaning step is a step of performing cleaning to remove a salt, a reaction solvent, and the like contained in the polycondensation reaction product obtained by the polycondensation reaction.

In this cleaning step, preferably, the reaction solvent in the polycondensation reaction product is subjected to extraction cleaning by a known method using a solvent such as an alcohol, a ketone, an aromatic hydrocarbon, an aliphatic hydrocarbon, or water, and then the salt resulting from the desalting reaction in the polycondensation reaction product is removed by cleaning with preferably water.

In a specific operation, the polycondensation reaction product in pulverized, slurry, or wax form is transferred to a container equipped with a stirrer, and an operation of stirring cleaning with a cleaning solvent and filtration is repeated until the contents of the reaction solvent and the salt fall below the desired levels.

As an apparatus, for example, a combination of a cleaning tank with a pressure filter or a centrifuge, or a multifunctional filtration system capable of performing cleaning, filtration, and drying by itself may be used.

Specific examples, excluding water, of solvents for extraction cleaning of the reaction solvent include alcohols such as methanol, ethanol, propyl alcohol, isopropyl alcohol, butyl alcohol, isobutyl alcohol, sec-butyl alcohol, t-butyl alcohol, n-amyl alcohol, isoamyl alcohol, t-amyl alcohol, n-hexyl alcohol, cyclohexanol, n-octyl alcohol, and capryl alcohol; ketones such as acetone, methyl ethyl ketone, methyl n-propyl ketone, diethyl ketone, 2-hexanone, 3-hexanone, methyl-t-butyl ketone, di-n-propyl ketone, diisopropyl ketone, diisobutyl ketone, di-n-amyl ketone, diacetyl, acetylacetone, cyclohexanone, and benzophenone; aliphatic hydrocarbons including saturated aliphatic hydrocarbons such as n-hexane, 2methylheptane, 3methylheptane, 2,2-dimethylbutane, 2,3-dimethylbutane, n-heptane, 2-methylhexane, 3-methylhexane, 2,2-dimethylpentane, 2,3-dimethylpentane, 2,4-dimethylpentane, 3,3-dimethylpentane, 3-ethylpentane, 2,2,3-trimethylbutane, and cyclohexane and unsaturated hydrocarbons such as 1-hexene, 1-heptene, 1-octene, and cyclohexene; and aromatic hydrocarbons such as benzene, toluene, o-xylene, m-xylene, p-xylene, ethylbenzene, n-propylbenzene, cumene, n-butylbenzene, t-butylbenzene, styrene, and allylbenzene.

Of these, for example, methanol, ethanol, acetone, methyl ethyl ketone, xylene, and toluene are preferred, and acetone and methanol are particularly preferred in terms of operability and ease of distillation recovery of the reaction solvent after cleaning.

For the cleaning of the alkali metal salt such as potassium chloride resulting from the desalting polycondensation reaction, water is preferably used, or acidic water containing oxalic acid or acetic acid at a low concentration may be used.

For the conditions of this cleaning step, the amount of cleaning solvent used, the number of times of cleaning, and the cleaning temperature may be appropriately selected according to the amounts of residual reaction solvent and residual alkali metal salt desired to be removed.

The drying step is a step of drying the polycondensation reaction product obtained by the above cleaning step.

The water-containing polycondensation reaction product that has been through the cleaning is dried by a known method. As a dryer, a known apparatus such as an evaporator, a shelf-type oven, or a tumbler can be used.

The target water content is typically 0.5 wt % or less, preferably 0.4 wt % or less, still more preferably 0.3 wt % or less.

This drying step may be performed under any conditions as long as the temperature is equal to or lower than the melting point of the polycondensation reaction product and water can be removed. To avoid contact with air as much as possible, the drying step is preferably performed under reduced pressure in an inert gas (e.g., nitrogen or argon) atmosphere or under a stream of inert gas.

The molecular weight of the polyether nitrile produced by the production method according to the present invention is a molecular weight corresponding to a degree of polymerization at which the number of repetitions represented by general formula (5) is 94 or more.

The degree of polymerization of 94 or more is a value at which the polymer reduced viscosity of a parachlorophenol solution at 40° C. is 2 or more when the aromatic dihydroxy compound (I-a) is 4,4'-biphenol and the dihalobenzonitrile compound (II-a) is 2,6-dihalobenzonitrile.

The polycondensation reaction product dried in the above drying step is basically a powder; thus, to produce a molded article, this powder can be used to produce a molding material (pellets, chips, or the like). The method of producing a molding material by melting the polyether nitrile powder by heating is not particularly limited, but is preferably performed under exclusion of oxygen or in an inert atmosphere such as nitrogen.

For the production of a molding material such as pellets or chips, a melt-kneading apparatus such as a single-screw, twin-screw, or multi-screw extruder, a Banbury mixer, a kneader, or a roller is typically used, but a molding material such as pellets or chips may be produced by cutting a sheet prepared using a compression molding machine as used in Examples described later.

An industrially preferred process in producing a molding material is as follows. The polyether nitrile powder obtained through polycondensation, pulverization, cleaning, and vacuum drying is directly transferred to, for example, a silo sealed with nitrogen gas or the like and stored there without being exposed to the outside air. When formed into a shape such as pellets or chips, the powder is transferred to an extruder together with nitrogen gas through a pipe without any treatment. The powder is then melt-kneaded in no contact with oxygen (air), and a molten polymer from a die is pelletized by cutting in water or water-cooled cutting of a strand.

For the conditions of the process of producing this molding material (pellets or chips), in melt processing, the operation described above is performed at a temperature sufficient to melt the polymer. The upper limit of the temperature in the melt processing is 500° C. or lower. The polyether nitrile powder used in Examples, which is obtained using biphenol, has a melting point of 364° C. and thus is preferably processed at a temperature higher than the melting point, 380° C. or higher. The upper limit of the temperature is preferably 480° C. or lower, more preferably 450° C. or lower, still more preferably 430° C. or lower, particularly preferably 400° C. or lower.

The polyether nitrile powder or molding material obtained by the production method according to the present invention may be mixed with at least one selected from the group consisting of a thermoplastic resin material (A), an additive (B), and a filler (C) to provide a polyether nitrile resin composition.

The polyether nitrile resin composition can be produced in the same manner as the above-described process of producing a molding material. For the mixing of the components, methods such as 1) preliminarily mixing the polyether nitrile powder or preformed polyether nitrile molding material and other components ((A) to (C) above) and then transferring the mixture to an extruder, 2) preliminarily preparing molding materials of a plurality of polyether nitrile resin compositions having different compositions using the polyether nitrile powder or preformed polyether nitrile molding material and other components ((A) to (C) above), mixing the molding materials in predetermined amounts so as to give a desired content ratio, and then transferring the mixture to an extruder, 3) directly feeding the polyether nitrile powder or preformed polyether nitrile molding material and other components ((A) to (C) above) into an extruder can be employed, and these methods are preferably performed in an inert atmosphere.

Specific examples of the thermoplastic resin material (A) contained in the polyether nitrile resin composition include high-density polyethylene, medium-density polyethylene, isotactic polypropylene, acrylonitrile-butadiene-styrene (ABS) resin, acrylonitrile-styrene (AS) resin, acrylic resin, fluorocarbon resin (e.g., polytetrafluoroethylene), polyester, polycarbonate, polyarylate, aliphatic polyamide, aromatic polyamide, polysulfone, polyether sulfone, polyether ketone, polyether ether ketone, polyphenylene sulfide, polyetherimide, polyamide-imide, polyesterimide, and modified polyphenylene oxide.

Specific examples of the additive (B) contained in the polyether nitrile resin composition include hydrophilic agents, antioxidants, secondary antioxidants, flame retardants, flame retardant aids, plasticizers, lubricants, release agents, antifogging agents, weathering stabilizers, light stabilizers, hydrolysis resistance improvers, flowability improvers, UV absorbers, antistatic agents, metal deactivators, near-infrared absorbers, and colorants (dyes and pigments).

Specific examples of the filler (C) contained in the polyether nitrile resin composition include various metal powders, powders of inorganic acid metal salts (e.g., calcium carbonate, zinc borate, calcium borate, zinc stannate, calcium sulfate, and barium sulfate), powders of metal oxides (e.g., magnesium oxide, iron oxide, titanium oxide, zinc oxide, and alumina), powders of metal hydroxides (e.g., aluminum hydroxide, magnesium hydroxide, zirconium hydroxide, and alumina hydrate (boehmite)), powders of metal sulfides (e.g., zinc sulfide, molybdenum sulfide, and tungsten sulfide), silver nanowires, carbon fibers, glass fibers, carbon nanotubes, graphene, and ceramic materials such as silica.

These (A) to (C) can be mixed in an appropriate amount depending on the intended use.

To obtain a polyether nitrile resin composition molding material having high melt flowability by melt-molding the polyether nitrile resin composition in the present invention under exclusion of oxygen or in an inert atmosphere, the amount of (A) to (C) is preferably 90 wt % or less relative to the total weight of the polyether nitrile resin composition.

The polyether nitrile obtained by the method of the present invention can be processed into a molding material by the above-described method or subjected to the production of a molded article or a part using the molding material, and has heat resistance, chemical resistance, flame resistance, and high mechanical properties. The polyether nitrile can be used in, for example, electric and electronic applications such as personal computers and semiconductor parts, automotive applications such as gears, bearings, and housings around engines, or applications in the medical equipment and aerospace fields.

EXAMPLES

The present invention will now be described more specifically with reference to Examples, but it should be noted that the present invention is not limited to these Examples.

Analysis methods in the present invention are as follows.

(1) Method of Measuring Reduced Viscosity $\eta_{red}$ (dL/g)

As described above, 0.1 g of a sample was dissolved in about 5 g of parachlorophenol at 180° C., and the solution was transferred to a 10 mL measuring flask. The flask was made up to volume at 40° C., and the resultant was weighed out with a 5 mL whole pipette and put into an Ostwald tube (capillary tube, 0.75 mm). This was allowed to stand in a constant-temperature bath at 40.0° C. for 15 minutes, and a flow time T was measured to make a calculation by the following calculation formula.

[Calculation Formula]

$$\text{Reduced viscosity } \eta_{red} = \{(T/T_0) - 1\}/C$$

C: concentration (g/dL) of solution

T: flow time (s) of sample solution $T_0$: flow time (s) of parachlorophenol (2) Thermal Properties: Melting Point and Glass Transition Temperature (Tg)

Using a differential scanning calorimeter (DSC-60, manufactured by Shimadzu Corporation), thermal properties of a sample were measured under the following conditions.

Conditions: sample, about 10 mg; nitrogen flow rate, 50 mL/min; temperature change range, 50° C. to 450° C.; temperature change rate, 10° C./min (3) Analysis of Raw Material Impurities The contents of the aromatic dihydroxy compound (I-a), the aromatic monohydroxy compound (I-b), and other impurities contained in the aromatic dihydroxy compound composition (I) and the contents of the dihalobenzonitrile compound (II-a), the monohalobenzonitrile compound (II-b), and other impurities contained in the dihalobenzonitrile compound composition (II) were quantitatively determined by high-performance liquid chromatography (hereinafter referred to as HPLC).

Example 1

In a four-necked 3 L reactor equipped with a mechanical stirrer with a torque meter, a thermometer, a dry nitrogen inlet, and a reflux condenser, 298.45 g of 99.90 wt % pure 2,6-dichlorobenzonitrile (hereinafter referred to as "DCBN") containing 40 ppm of 2-chlorobenzonitrile (hereinafter referred to as "MCBN"), 323.08 g of 99.95 wt % pure 4,4'-biphenol (hereinafter "BP") containing 25 ppm of phenol (hereinafter referred to as "PhOH"), 251.79 g (1.822 mol) of anhydrous potassium carbonate, 60 g of toluene, and 1562 g of anhydrous sulfolane were loaded.

The content of PhOH is 0.005 mol % relative to the total number of moles of BP and PhOH, and the content of MCBN is 0.005 mol % relative to the total number of moles of DCBN and MCBN.

This mixture was heated from room temperature under a stream of nitrogen, and with stirring at 250 rpm, the temperature was increased to 160° C. with heating under reflux. At 130° C. or higher, carbon dioxide was evolved from the reaction of potassium carbonate and biphenol. After 3 hours at 160° C., the oligomerization reaction of "DCBN" and "BP" was completed, and the cooling water in the reflux condenser was then replaced with warm water to remove water and toluene through an outlet, whereby the temperature was raised to 220° C. to effect polymerization. At 1.5 hours after the temperature was raised to 220° C., sampling was performed, and the polymerization was further continued for 30 minutes, at which point the reaction was terminated, and a polycondensation reaction product was taken out from the bottom of the reactor and allowed to cool and solidify.

After this solid product was pulverized with a Waring blender, this substance was washed several times with acetone and distilled water and dried in a vacuum oven at 120° C. for 16 hours to obtain a polyether nitrile powder (yield, 95%).

The polymer powder had a reduced viscosity of 5.98.

For comparison, a polymer powder obtained by processing, in the same manner as above, a polycondensation reaction product sampled at 1.5 hours after the reaction temperature was raised to 220° C. had a reduced viscosity of 2.52.

Table 1 shows details of the aromatic dihydroxy compound and the dihalobenzonitrile compound used and reduced viscosities measured after polymerization.

Examples 2 to 6 and Comparative Examples 1 to 4

A polymer powder was obtained by the same operation as in Example 1 except that the aromatic dihydroxy compound composition (I) and the dihalobenzonitrile compound composition (II) used were changed as shown in Table 1, and measured for reduced viscosity.

The results are shown in Table 1.

TABLE 1

| | Item | Unit | Example 1 | Example 2 | Example 3 | Example 4 | Example 5 | Example 6 |
|---|---|---|---|---|---|---|---|---|
| Aromatic dihydroxy compound composition (I) | Amount loaded | g | 323.08 | 323.08 | 323.08 | 323.08 | 323.08 | 323.08 |
| | Aromatic dihydroxy compound (I-a) | — | BP | BP | BP | BP | BP | BP |
| | Aromatic dihydroxy compound (I-a) content (vs entire aromatic dihydroxy compound composition (I)) | wt % | 99.95 | 99.39 | 99.95 | 99.65 | 99.39 | 99.39 |
| | Aromatic monohydroxy compound (I-b) | — | PhOH | PhOH | PhOH | PhOH | PhOH | PhOH |
| | Aromatic monohydroxy compound (I-b) content | wt % | 0.00 | 0.51 | 0.00 | 0.25 | 0.51 | 0.51 |
| | (vs entire aromatic dihydroxy compound composition (I)) | ppm | 25 | 5100 | 25 | 2500 | 5100 | 5100 |
| | Other impurities content | wt % | 0.05 | 0.10 | 0.05 | 0.10 | 0.10 | 0.10 |
| | Aromatic dihydroxy compound (I-a) content (vs total amount of (I-a) and (I-b)) | mol % | 99.995 | 99.000 | 99.995 | 99.500 | 99.000 | 99.000 |
| | Aromatic monohydroxy compound (I-b) content (vs total amount of (I-a) and (I-b)) | mol % | 0.005 | 1.000 | 0.005 | 0.500 | 1.000 | 1.000 |
| Dihalo-benzonitrile compound composition (II) | Amount loaded | g | 298.45 | 298.45 | 298.45 | 298.45 | 298.45 | 298.45 |
| | Dihalobenzonitrile compound (II-a) | — | DCBN | DCBN | DCBN | DCBN | DCBN | DCBN |
| | Dihalobenzonitrile compound (II-a) content (vs entire dihalobenzonitrile compound composition (II)) | wt % | 99.90 | 99.90 | 99.05 | 99.05 | 99.45 | 99.05 |
| | Monohalobenzonitrile compound (II-b) | — | MCBN | MCBN | MCBN | MCBN | MCBN | MCBN |
| | Monohalobenzonitrile compound (II-b) content | wt % | 0.00 | 0.00 | 0.80 | 0.30 | 0.40 | 0.80 |
| | (vs entire dihalobenzonitrile compound composition (II)) | ppm | 40 | 40 | 8000 | 8000 | 4000 | 8000 |
| | Other impurities content | wt % | 0.10 | 0.10 | 0.15 | 0.15 | 0.15 | 0.15 |
| | Dihalobenzonitrile compound (II-a) content (vs total amount of (II-a) and (II-b)) | mol % | 99.995 | 99.995 | 99.000 | 99.000 | 99.500 | 99.000 |
| | Monohalobenzonitrile compound (II-b) content (vs total amount of (II-a) and (II-b)) | mol % | 0.005 | 0.005 | 1.000 | 1.000 | 0.500 | 1.000 |

TABLE 1-continued

| | | | | | | | | |
|---|---|---|---|---|---|---|---|---|
| Polyether nitrile | Reduced viscosity η at 1.5 hr after 220° C. polymerization | (dl/g) | 2.52 | 2.34 | 1.84 | — | — | — |
| | Reduced viscosity η at 2 hr after 220° C. polymerization | (dl/g) | 5.98 | 3.99 | 2.11 | 2.13 | 2.74 | 2.09 |

| | Item | Unit | Comparative Example 1 | Comparative Example 2 | Comparative Example 3 | Comparative Example 4 |
|---|---|---|---|---|---|---|
| Aromatic dihydroxy compound composition (I) | Amount loaded | g | 323.08 | 323.08 | 323.08 | 324.08 |
| | Aromatic dihydroxy compound (I-a) | — | BP | BP | BP | BP |
| | Aromatic dihydroxy compound (I-a) content (vs entire aromatic dihydroxy compound composition (I)) | wt % | 99.90 | 98.88 | 98.88 | 98.88 |
| | Aromatic monohydroxy compound (I-b) | — | PhOH | PhOH | PhOH | PhOH |
| | Aromatic monohydroxy compound (I-b) content (vs entire aromatic dihydroxy compound composition (I)) | wt % | 0.00 | 1.02 | 1.02 | 1.02 |
| | | ppm | 25 | 10200 | 10200 | 10200 |
| | Other impurities content | wt % | 0.10 | 0.10 | 0.10 | 0.10 |
| | Aromatic dihydroxy compound (I-a) content (vs total amount of (I-a) and (I-b)) | mol % | 99.995 | 98.000 | 98.000 | 98.000 |
| | Aromatic monohydroxy compound (I-b) content (vs total amount of (I-a) and (I-b)) | mol % | 0.005 | 2.000 | 2.000 | 2.000 |
| Dihalo-benzonitrile compound composition (II) | Amount loaded | g | 298.45 | 298.45 | 298.45 | 298.45 |
| | Dihalobenzonitrile compound (II-a) | — | DCBN | DCBN | DCBN | DCBN |
| | Dihalobenzonitrile compound (II-a) content (vs entire dihalobenzonitrile compound composition (II)) | wt % | 98.25 | 99.05 | 98.25 | 99.90 |
| | Monohalobenzonitrile compound (II-b) | — | MCBN | MCBN | MCBN | MCBN |
| | Monohalobenzonitrile compound (II-b) content (vs entire dihalobenzonitrile compound composition (II)) | wt % | 1.60 | 0.80 | 1.60 | 0.00 |
| | | ppm | 16000 | 8000 | 16000 | 40 |
| | Other impurities content | wt % | 0.15 | 0.15 | 0.15 | 0.10 |
| | Dihalobenzonitrile compound (II-a) content (vs total amount of (II-a) and (II-b)) | mol % | 98.000 | 99.000 | 98.000 | 99.995 |
| | Monohalobenzonitrile compound (II-b) content (vs total amount of (II-a) and (II-b)) | mol % | 2.000 | 1.000 | 2.000 | 0.005 |
| Polyether nitrile | Reduced viscosity η at 1.5 hr after 220° C. polymerization | (dl/g) | — | — | — | — |
| | Reduced viscosity η at 2 hr after 220° C. polymerization | (dl/g) | 1.12 | 1.43 | 1.10 | 1.67 |

As shown in Table 1, it has become clear that in Examples 1 to 6, which are each the production method according to the present invention and in which the aromatic dihydroxy compound composition (I) containing, as an impurity, the aromatic monohydroxy compound (I-b) in an amount ranging from 1 to 0.005 mol % relative to the total amount of the aromatic dihydroxy compound (I-a) and the aromatic monohydroxy compound (I-b) and the dihalobenzonitrile compound composition (II) containing, as an impurity, the monohalobenzonitrile compound (II-b) in an amount ranging from 1 to 0.005 mol % relative to the total amount of the dihalobenzonitrile compound (II-a) and the monohalobenzonitrile compound (II-b) are used, as compared with Comparative Examples 1 to 4, the reduced viscosity of the resulting polymer becomes 2 or more within a polymerization time of 2 hours.

The production method according to the present invention in which the contents of the aromatic monohydroxy compound (I-b) and the monohalobenzonitrile compound (II-b) are within the above ranges has been confirmed to be an excellent production method by which a high-molecular-weight polyether nitrile that is polymerized at a high rate and achieves a reduced viscosity of 2 or more can be obtained.

The invention claimed is:

1. A method for producing a polyether nitrile, comprising allowing an aromatic dihydroxy compound composition (I) and a dihalobenzonitrile compound composition (II) to undergo a polycondensation reaction in the presence of a basic compound, wherein the aromatic dihydroxy compound composition (I) includes an aromatic dihydroxy compound (I-a) and an aromatic monohydroxy compound (I-b), and contains (I-a) in an amount ranging from 99.0 to 99.995 mol % and (I-b) in an amount ranging from 1 to 0.005 mol % relative to a total amount of (I-a) and (I-b), and the dihalobenzonitrile compound composition (II) includes a dihalobenzonitrile compound (II-a) and a monohalobenzonitrile compound (II-b), and contains (II-a) in an amount ranging from 99.0 to 99.995 mol % and (II-b) in an amount ranging from 1 to 0.005 mol % relative to a total amount of (II-a) and (II-b).

2. The method for producing a polyether nitrile according to claim 1, wherein the aromatic dihydroxy compound (I-a) is a compound represented by general formula (1) below, the aromatic monohydroxy compound (I-b) is a compound represented by general formula (2) below, the dihalobenzonitrile compound (II-a) is a compound represented by general formula (3) below, and the monohalobenzonitrile compound (II-b) is a compound represented by general formula (4) below:

$$HO—R—OH \quad (1)$$

wherein R represents a divalent group represented by general formula (1a) below or general formula (1b) below;

(1a)

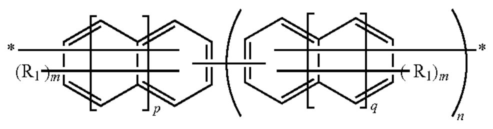

wherein each $R_1$ independently represents a linear or branched alkyl group having 1 to 6 carbon atoms, a cyclic alkyl group having 5 or 6 carbon atoms, a phenyl group, a phenoxy group, or a phenylalkyl group having 7 to 10 carbon atoms, m represents an integer of 0 to 4, n represents 0 or 1, p and q each independently represent 0, 1, or 2, and each * represents a bonding position;

(1b)

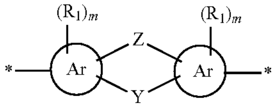

wherein $R_1$ and m are as defined in general formula (1a), Y represents an oxygen atom, a sulfur atom, a sulfonyl group, a carbonyl group, an alkylidene group having 1 to 15 carbon atoms, a fluorine-containing alkylidene group having 2 to 15 carbon atoms, a cycloalkylidene group having 5 to 15 carbon atoms, a phenylmethylidene group, a phenylethylidene group, a phenylene group, or a fluorenylidene group, Z represents an oxygen atom, a sulfur atom, or non-bridging, each Ar independently represents an aryl group having 6 to 8 carbon atoms, and each * represents a bonding position;

(2)

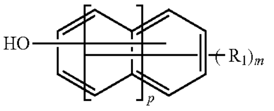

wherein $R_1$, m, and p are as defined in general formula (1a);

(3)

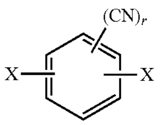

wherein each X independently represents a halogen atom, and r represents an integer of 1 to 4;

(4)

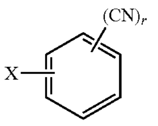

wherein X and r are as defined in general formula (3).

3. The method for producing a polyether nitrile according to claim 2, wherein R in the compound represented by general formula (1) is general formula (1a') below or general formula (1a") below, p in the compound represented by general formula (2) is 0, and r in the compound represented by general formula (3) and the compound represented by general formula (4) is 1;

(1a')

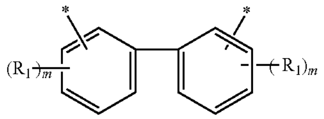

wherein $R_1$, m, and * are as defined in general formula (1a);

(1a")

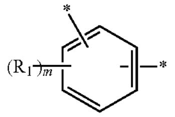

wherein $R_1$, m, and * are as defined in general formula (1a).

4. The method for producing a polyether nitrile according to claim 2, wherein the aromatic dihydroxy compound (I-a) is 4,4'-biphenol, the aromatic monohydroxy compound (I-b) is phenol, the dihalobenzonitrile compound (II-a) is 2,6-dichlorobenzonitrile, and the monohalobenzonitrile compound (II-b) is 2-chlorobenzonitrile.

5. The method for producing a polyether nitrile according to claim 1, wherein in the aromatic dihydroxy compound composition (I), a content of the aromatic dihydroxy compound (I-a) relative to the entire aromatic dihydroxy compound composition (I) is 99.0 wt % or more, and in the dihalobenzonitrile compound composition (II), a content of the dihalobenzonitrile compound (II-a) relative to the entire dihalobenzonitrile compound composition (II) is 99.0 wt % or more.

6. The method for producing a polyether nitrile according to claim 1, wherein a resulting polyether nitrile has a reduced viscosity of 2.0 or more.

7. The method for producing a polyether nitrile according to claim 2, wherein a resulting polyether nitrile has a reduced viscosity of 2.0 or more.

8. The method for producing a polyether nitrile according to claim 3, wherein a resulting polyether nitrile has a reduced viscosity of 2.0 or more.

9. The method for producing a polyether nitrile according to claim 4, wherein a resulting polyether nitrile has a reduced viscosity of 2.0 or more.

10. The method for producing a polyether nitrile according to claim 5, wherein a resulting polyether nitrile has a reduced viscosity of 2.0 or more.

* * * * *